United States Patent [19]
Lin et al.

[11] Patent Number: 5,458,660
[45] Date of Patent: Oct. 17, 1995

[54] FUEL COMPOSITIONS

[75] Inventors: Jiang-Jen Lin; Pen-Chung Wang; Sarah L. Weaver, all of Houston, Tex.

[73] Assignee: Shell Oil Company, Houston, Tex.

[21] Appl. No.: 308,726

[22] Filed: Sep. 19, 1994

[51] Int. Cl.$^6$ .................................. C10L 1/18; C10L 1/22
[52] U.S. Cl. .................................. 44/340; 548/551
[58] Field of Search ................. 44/340; 548/551

[56] References Cited

U.S. PATENT DOCUMENTS

| | | |
|---|---|---|
| 3,438,757 | 4/1969 | Honnen et al. . |
| 3,574,576 | 4/1971 | Honnen et al. . |
| 3,753,670 | 8/1973 | Strang et al. . |
| 3,756,793 | 9/1973 | Robinson . |
| 4,160,648 | 7/1979 | Lewis et al. . |
| 4,191,537 | 3/1980 | Lewis et al. . |
| 4,231,759 | 11/1980 | Udelhofen et al. . |
| 4,236,020 | 11/1980 | Lewis et al. . |
| 4,270,930 | 6/1981 | Campbell et al. . |
| 4,288,612 | 9/1981 | Lewis et al. . |
| 4,612,335 | 9/1986 | Cuscurida et al. . |
| 4,713,463 | 12/1987 | Chaudhuri et al. . |
| 4,801,400 | 1/1989 | Login et al. . |
| 4,810,261 | 3/1989 | Sung et al. . |
| 4,852,993 | 8/1989 | Sung et al. . |
| 4,852,993 | 8/1989 | Sung et al. . |
| 4,881,945 | 11/1989 | Buckley, III . |
| 4,883,826 | 11/1989 | Marugg et al. . |
| 4,936,868 | 6/1990 | Johnson . |
| 4,968,321 | 11/1990 | Sung et al. . |
| 4,973,414 | 11/1990 | Nerger et al. . |
| 4,985,047 | 1/1991 | Sung et al. . |
| 5,061,291 | 10/1991 | Sung . |
| 5,123,932 | 6/1992 | Rath et al. . |
| 5,147,414 | 9/1992 | Powers, III et al. . |
| 5,352,251 | 10/1994 | Lin et al. ............... 44/340 |

*Primary Examiner*—Jacqueline V. Howard

[57] ABSTRACT

The present invention is directed to the use of cyclic amide compounds containing multiple polyether alcohol backbones as additives in fuel compositions having a major amount of a mixture of hydrocarbons in the gasoline boiling range and a minor amount of one or more cyclic amide compounds containing multiple polyether backbones. The invention is also directed to the use of these cyclic amide alkoxylate compounds for decreasing intake valve deposits, controlling octane requirement increases and reducing octane requirement. The invention is further directed to cyclic amide compounds containing multiple polyether backbones.

37 Claims, No Drawings

FUEL COMPOSITIONS

BACKGROUND OF THE INVENTION

1. Field of the Invention

The present invention relates to the use of cyclic amide compounds containing multiple polyether alcohol backbone as additives in fuel compositions and the use of these compounds to decrease intake valve deposits, control octane requirement increases and reduce octane requirement. The present invention further relates to a class of cyclic amides compounds containing multiple polyether alcohol backbones.

2. Background

The accumulation of deposits on intake valves of internal combustion engines presents a variety of problems. The accumulation of such deposits is characterized by overall poor driveability including hard starting, stalls, and stumbles during acceleration and rough engine idle.

Many additives are known which can be added to hydrocarbon fuels to prevent or reduce deposit formation, or remove or modify formed deposits, in the combustion chamber and on adjacent surfaces such as intake valves, ports, and spark plugs, which in turn causes a decrease in octane requirement.

Continued improvements in the design of internal combustion engines, e.g., fuel injection and carburetor engines, bring changes to the environment of such engines thereby creating a continuing need for new additives to control the problem of inlet system deposits and to improve driveability which is usually related to deposits.

It would be an advantage to have fuel compositions which would reduce the formation of deposits and modify existing deposits that are related to octane requirement increase and poor driveability in modern engines which burn hydrocarbon fuels.

SUMMARY OF THE INVENTION

The present invention is directed to the use of cyclic amide compounds containing multiple polyether alcohol backbones as additives in fuel compositions comprising a major amount of a mixture of hydrocarbons in the gasoline boiling range and a minor amount of one or more cyclic amide compounds containing multiple polyether alcohol backbones of Formula I:

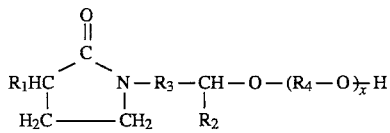
(I)

wherein $R_1$ and $R_2$ are each independently selected from hydrogen, hydrocarbyl of 1 to 100 carbon atoms, substituted hydrocarbyl of 1 to 100 carbon atoms and polyoxyalkylene alcohol of Formula II:

(II)

wherein $R_5$ is selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selected from the group consisting of hydrocarbyl of 1 to 100 carbon atoms and substituted hydrocarbyl of 1 to 100 carbon atoms; each $R_4$ is independently selected from hydrocarbyl of 2 to 100 carbon atoms and substituted hydrocarbyl of 2 to 100 carbon atoms; x is from 1 to 50 and the weight average molecular weight of the additive compound is at least 600.

The invention is also directed to the use of these cyclic amide compounds containing multiple polyether alcohol backbones for decreasing intake valve deposits, controlling octane requirement increases and reducing octane requirement.

DESCRIPTION OF THE PREFERRED EMBODIMENTS

Compounds

The compounds of the present invention, broadly expressed as cyclic amide alkoxylates containing multiple polyether alcohol backbones, are a new class of additives useful for hydrocarbon fuels, e.g., fuels in the gasoline boiling range, for preventing deposits in engines, controlling octane requirement increases and reducing octane requirement, while also decomposing during combustion to environmentally acceptable products. The compounds produce very little residue and are miscible with carriers and other detergents. Non-limiting illustrative embodiments of the compounds useful as additives in the instant invention include those of Formula I:

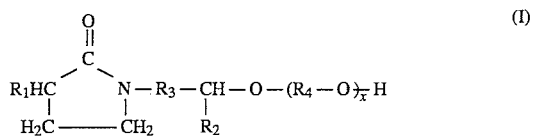
(I)

In Formula I, $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of Formula II:

(II)

wherein $R_5$ is selected from the group consisting of hydrocarbyl of 2 to 100 carbon atoms, substituted hydrocarbyl of 2 to 100 carbon atoms and y is from 1 to 50; with the proviso that at least one of $R_1$ and $R_2$ must be polyoxyalkylene alcohol.

When $R_1$ or $R_2$ are hydrocarbyl or substituted hydrocarbyl, they will preferably be hydrocarbyl or substituted hydrocarbyl of 1 to 50 carbon atoms. When $R_1$ or $R_2$ are hydrocarbyl of a relatively high number of carbon atoms, i.e., greater than about 50 carbon atoms, $R_1$ or $R_2$ will be represented by polymeric hydrocarbyls derived from polyisobutylene, polybutene, polypropylene or poly-alphaolefin. As used herein, the term "hydrocarbyl" represents a radical formed by the removal of one or more hydrogen atoms from a carbon atom of a hydrocarbon (not necessarily the same carbon atom). Useful hydrocarbyls are aliphatic, aromatic, substituted, unsubstituted, acyclic or cyclic. Preferably, the hydrocarbyls are aryl, alkyl, alkenyl or cycloalkyl and are straight-chain or branched-chain. Representative hydrocarbyls include methyl, ethyl, butyl, pentyl, methylpentyl, hexenyl, ethylhexyl, dimethylhexyl, octamethylene, octenylene, cyclooctylene, methylcyclooctylene, dimethylcyclooctyl, isooctyl, dodecyl, hexadecenyl, octyl, eicosyl, hexacosyl, triacontyl and phenylethyl. When the hydrocarbyl is substituted, it contains a functional group such as carbonyl, carboxyl, nitro, amino, hydroxy (e.g. hydroxyethyl), oxy, cyano, sulfonyl, and sulfoxyl. The majority of the atoms, other than hydrogen, in substituted hydrocarbyls are carbon, with the heteroatoms (i.e., oxygen, nitrogen, sulfur) representing only a minority, 33% or less, of the total non-hydrogen atoms present.

More preferably, when $R_1$ or $R_2$ are selected from hydrocarbyl and substituted hydrocarbyl, they will preferably be hydrocarbyl or substituted hydrocarbyl of 1 to 20 carbon atoms. Even more preferably, $R_1$ or $R_2$ will be alkyl of 1 to 20 carbon atoms and most preferably alkyl of 1 to 8 carbon atoms.

As noted, at least one of $R_1$ and $R_2$ must be polyoxyalkylene alcohol of Formula II:

wherein each $R_5$ is independently selected from the group consisting of hydrocarbyl, as defined hereinbefore, of 2 to 100 carbon atoms and substituted hydrocarbyl, as defined hereinbefore, of 2 to 100 carbon atoms and y is from 1 to 50. Preferably each $R_5$ is independently selected from hydrocarbyl of 2 to 50 carbon atoms, more preferably alkyl of 2 to 20 carbon atoms. Preferred compounds are those in which $R_5$ is hydrocarbyl of 2 to 4 carbon atoms, especially 4 carbon atoms. When $R_5$ is hydrocarbyl or substituted hydrocarbyl of a relatively high number of carbon atoms, i.e., greater than about 50 carbon atoms, $R_5$ will be represented by polymeric hydrocarbyls derived from polyisobutylene, polybutene, polypropylene or polyalphaolefin.

Particularly preferred compounds of Formula I are those in which $R_5$ is hydrocarbyl (geminal or vicinal) of formula:

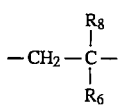

or

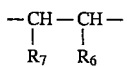

$R_6$, $R_7$ and $R_8$ are each independently selected from the group consisting of hydrogen, hydrocarbyl, as defined hereinbefore, of 1 to 98 carbon atoms and substituted hydrocarbyl, as defined hereinbefore, of 1 to 98 carbon atoms. Preferred $R_6$, $R_7$ and $R_8$ groups are hydrogen, hydrocarbyl of 1 to 18 carbon atoms and substituted hydrocarbyl of 1 to 18 carbon atoms. $R_7$ and $R_6$, or alternatively $R_6$ and $R_8$, may be taken together to form a divalent linking hydrocarbyl group of 3 to 12 carbon atoms.

The most preferred compounds of Formula I are those in which when $R_1$ and/or $R_2$ are polyoxyalkylene alcohol, each $R_5$ is hydrocarbyl as represented by Formula III above wherein $R_8$ is hydrogen and $R_6$ is independently selected from hydrogen, alkyl of 1 to 18 carbon atoms or oxy-substituted hydrocarbyl of 1 to 18 carbon atoms, particularly those compounds where $R_8$ is hydrogen and $R_6$ is independently hydrogen or alkyl of 1 to 2 carbon atoms, especially those compounds where $R_8$ is hydrogen and $R_6$ is alkyl of 2 carbon atoms.

When $R_6$ is oxy-substituted hydrocarbyl of 1 to 18 carbon atoms, $R_6$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

In Formula II above, y is from 1 to 50, preferably from 1 to 40, and even more preferably from 1 to 26. Those of ordinary skill in the art will recognize that when the compounds of Formula I in which $R_1$ and/or $R_2$ are polyoxyalkylene alcohol are used in a composition, y will not have a fixed value but will instead be represented by a range of different values. As used in this specification, y is considered to be a (number) average of the various values of y that are found in a given composition, which number has been rounded to the nearest integer. The range of y was determined by the gel permeation chromatography (GPC) analysis in the various examples and is indicated by the polydispersity (polydispersity=molecular weight based on the weight average divided by the molecular weight based on the number average).

When y is greater than 1, the individual $R_5$'s are the same or different. For example, if y is 20, each $R_5$'s can be alkyl of four carbon atoms. Alternatively, the $R_5$'s can differ and for instance, independently be alkyl from two to four carbon atoms. When the $R_5$'s differ, they may be present in blocks, i.e., all y groups in which $R_5$ is alkyl of three carbon atoms will be adjacent, followed by all y groups in which $R_5$ is alkyl of two carbon atoms, followed by all y groups in which $R_5$ is alkyl of four carbon atoms. When the $R_5$'s differ, they may also be present in any random distribution.

$R_3$ is selected from hydrocarbyl, as defined hereinbefore, of 1 to 100 carbon atoms and substituted hydrocarbyl, as defined hereinbefore, of 1 to 100 carbon atoms. Preferably $R_3$ is selected from hydrocarbyl of 1 to 20 carbon atoms and substituted hydrocarbyl of 1 to 20 carbon atoms. More preferably, $R_3$ is selected from alkyl of 1 to 14 carbon atoms and most preferably 1 to 3 carbon atoms. When $R_3$ is hydrocarbyl of a relatively high number of carbon atoms, i.e., greater than about 50 carbon atoms, $R_3$ will be represented by polymeric hydrocarbyls derived from polyisobutylene, polybutene, polypropylene or poly-alphaolefin.

Each $R_4$ is independently selected from hydrocarbyl, as defined hereinbefore, of 2 to 100 carbon atoms and substituted hydrocarbyl, as defined hereinbefore, of 2 to 100 carbon atoms. Preferably each $R_4$ is independently selected from hydrocarbyl of 2 to 50 carbon atoms and substituted hydrocarbyl of 2 to 50 carbon atoms, more preferably of 2 to 20 carbon atoms and most preferably 2 to 4 carbon atoms. When $R_4$ is hydrocarbyl of a relatively high number of carbon atoms, i.e., greater than about 50 carbon atoms, $R_4$ will be represented by polymeric hydrocarbyls derived from polyisobutylene, polybutene, polypropylene or polyalphaolefin.

Particularly preferred compounds of Formula I are those in which $R_4$ is hydrocarbyl (geminal or vicinal) of formula:

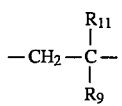

or

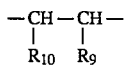

wherein $R_9$, $R_{10}$ and $R_{11}$ are each independently hydrogen, hydrocarbyl, as defined hereinbefore, of 1 to 98 carbon atoms or substituted hydrocarbyl, as defined hereinbefore, of 1 to 98 carbon atoms. Preferred $R_9$, $R_{10}$ and $R_{11}$ groups are hydrogen, hydrocarbyl of 1 to 18 carbon atoms and substituted hydrocarbyl of 1 to 18 carbon atoms. $R_{10}$ and $R_9$, or alternatively $R_9$ and $R_{11}$, may be taken together to form a divalent linking hydrocarbyl group of 3 to 12 carbon atoms.

The most preferred compounds of Formula I are those in which $R_4$ is hydrocarbyl as represented by Formula V above wherein $R_{11}$ is hydrogen and $R_9$ is independently hydrogen, alkyl of 1 to 18 carbon atoms or oxy-substituted hydrocarbyl of 1 to 18 carbon atoms, particularly those compounds where $R_{11}$ is hydrogen and $R_9$ is independently hydrogen or alkyl of 1 to 2 carbon atoms, especially those compounds where $R_{11}$ is hydrogen and $R_9$ is alkyl of two carbon atoms.

When $R_9$ is oxy-substituted hydrocarbyl of 1 to 18 carbon atoms, $R_9$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

In Formula I, x is from 1 to 50, preferably from 1 to 40, and even more preferably from 1 to 26. Those of ordinary skill in the art will recognize that when the compounds of Formula I are utilized in a composition, x will not have a fixed value but will instead be represented by a range of different values. As used in this specification, x is considered to be a (number) average of the various values of x that are found in a given composition, which number has been rounded to the nearest integer and x is considered to be a (number) average of the various values of x that are found in a given composition, which number has been rounded to the nearest integer. This is indicated in the various examples by the polydispersity (polydispersity=molecular weight based on the weight average divided by the molecular weight based on the number average).

When x is greater than 1, the individual $R_4$'s are the same or different. For example, if x is 20, each $R_4$ can be alkyl of four carbon atoms. Alternatively, the $R_4$'s can differ and for instance, independently be alkyl from two to four carbon atoms. When the $R_4$'s differ, they may be present in blocks, i.e., all x groups in which $R_4$ is alkyl of three carbon atoms will be adjacent, followed by all x groups in which $R_4$ is alkyl of two carbon atoms, followed by all x groups in which $R_4$ is alkyl of four carbon atoms. When the $R_4$'s differ, they may also be present in any random distribution.

In one of the most preferred embodiments of the present invention, $R_1$ will be polyoxyalkylene alcohol of Formula II, $R_2$ will be hydrogen, each $R_4$ and $R_5$ will independently selected from alkyl of 2 to 4 carbon atoms and x and y will each be from 1 to 26.

When $R_1$ is polyoxyalkylene alcohol of Formula II, preferably the sum of the values of x and y will not exceed 40, more preferably, the sum of the values of x and y will not exceed 26.

In a more preferred embodiment when $R_1$ is polyoxyalkylene alcohol of Formula II, x will be from 1 to 13 and y will be from 1 to 13.

The present invention is also directed to compounds of Formula I wherein $R_1$, $R_2$, $R_3$, $R_4$ and x are as defined hereinbefore.

The compounds of Formula I have a total weight average molecular weight of at least 600. Preferably, the total weight average molecular weight is from about 800 to about 4000, even more preferably from about 800 to about 2000.

Typical compounds represented by Formula I and the initiators used to prepare each include those listed by structure in Table 1.

| Initiator | Product |
|---|---|
| HO—CH₂—CH₂—C(—H)(—C(=O)—CH₂—CH₂—)N—CH₂—CH₂—OH (with H₂C—CH₂ ring) | H—(OCHCH₂)ᵧ—O—CH₂—CH₂—C(—H)(—C(=O)—CH₂—CH₂—)N—CH₂—CH₂—O—(CH₂CHO)ₓ—H, with CH₂/CH₃ side chains; wherein x is from 1 to 26 and y is from 1 to 26. |
| HO—CH₂—CH₂—C(—H)(—C(=O)—CH₂—CH₂—)N—CH₂—CH₂—CH₂—OH (with H₂C—CH₂ ring) | H—(OCHCH₂)ᵧ—O—CH₂—CH₂—C(—H)(—C(=O)—CH₂—CH₂—)N—CH₂—CH₂—CH₂—O—(CH₂CHO)ₓ—H, with CH₂/CH₃ side chains; wherein x is from 1 to 26 and y is from 1 to 26. |

The compounds of Formula I are illustratively prepared by alkoxylation, i.e., reacting an initiator selected from cyclic amidoalcohols or cyclic amides with one or more epoxides in the presence of a potassium compound.

In one embodiment of the present invention, the compounds of Formula I are prepared using one or more epoxides and cyclic amidoalcohol initiators represented by Formula VII:

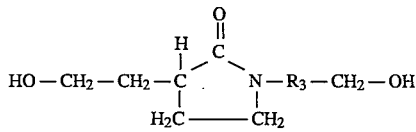
(VII)

wherein $R_3$ is as defined hereinbefore. Non-limiting examples of cyclic amidoalcohol initiators which are employed include 1,3-bis-2-hydroxyethyl-pyrolidinone, 1-hydroxypropyl-3-hydroxyethyl-pyrolidinone and 1-hydroxybutyl-3-hydroxyethyl-pyrolidinone.

The cyclic amidoalcohol initiators utilized can also be prepared by any of the methods known and described in the art. For example, cyclic amidoalcohol initiators can be prepared by reacting spirodilactone of Formula VIII:

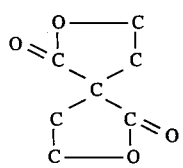
(VIII)

with aminoalcohol of Formula IX:

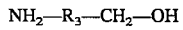
(IX)

Illustrative aminoalcohols for reacting with the spirodilactones to make the cyclic amidoalcohol initiators include: p-aminophenylmethanol, p-aminophenylethanol, 2-amino-1-butanol, 2-(2-aminoethoxy) ethanol, 2-amino-2-methyl-1-propanol, 3-amino-1-propanol, monoethanolamine and 1-amino-2-propanol.

The ratio of spirodilactone to aminoalcohol utilized in the preparation of the cyclic amidoalcohol initiators is typically 1:1 but may range from about 1:2 to about 2:1. In addition, the temperature of the reaction will generally be from about 80° C. to about 200° C., preferably from about 120° C. to about 130° C. The reaction time is not critical but will generally range from about 2 to about 4 hours, although longer or shorter times may be employed.

In an alternative embodiment of the present invention, the compounds of Formula I are prepared by reacting one or more epoxides and cyclic amidoalcohol initiators represented by Formula X:

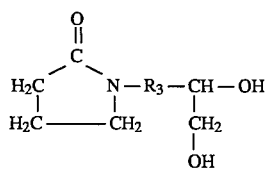
(X)

wherein $R_3$ is as defined hereinbefore.

The cyclic amidoalcohol initiators utilized can be prepared by any of the methods known and described in the art. For example, cyclic amidoalcohol initiators can be prepared by subjecting pyrrolidine-containing glycidyl ethers of Formula XI:

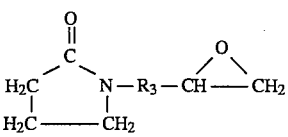
(XI)

wherein $R_3$ is as defined hereinbefore to acid or base hydrolysis. Non-limiting examples of the pyrrolidine-containing glycidyl ethers of Formula XI which are employed include N-(2,3-epoxypropyl)pyrrolidinone.

The amide-containing glycidyl ethers may be prepared by any of the methods known and described in the art, for example, in U.S. Pat. Nos. 4,713,463 and 4,801,400, each incorporated herein by reference. In U.S. Pat. No. 4,713,463, the amide-containing glycidyl ethers are prepared by adding epichlorohydrin to a 2 liter, 4-neck flask equipped with stirrer, reflux condenser, thermometer, and dropping funnel containing a mixture of sodium hydroxide and water while stirring. Tetrabutyl ammonium hydrogen sulfate is then introduced during agitation. The reaction mixture is stirred at room temperature for 15 minutes and the reaction exothermed to about 35° C. To the above reaction mixture a lactam is then added dropwise over a period of two hours. The resulting exothermic reaction is maintained between 35° C.–45° C. using ice water bath. After completion of the lactam addition, the reaction mixture is stirred for an additional 5 hours and filtered and filtrate collected. The precipitated salts is washed with methylene chloride. The filtrate and the methylene chloride washings are combined, dried over anhydrous sodium sulfate and again filtered to remove sodium sulfate. The filtrate is stripped and the residue placed in a distillation flask where, at a temperature of 30° C.–75° C. and about 0.25 mm Hg, the excess epichlorohydrin and the other low-boiling impurities is removed. The desired epoxide product is obtained at 90° C.–95° C. (0.2 mm Hg) and at a yield of 75%. The structure of the product can be confirmed by $^{13}C$ and H NMR data.

In U.S. Pat. No. 4,801,400, the amide-containing glycidyl ethers may be prepared by adding epibromohydrin and ethylene glycol dimethylether to a 5 liter flask equipped with a stirrer, condenser, thermometer and dropping funnel. Potassium pyrrolidone is then added to the mixture over a half hour period of time. The mixture is stirred for 48 hours at 25° C. Potassium bromide is removed by filtration and the product distilled. The fraction boiling at 87° C. to 100° C. at 0.07 to 0.1 mm Hg is collected as 201.8 g of product having a purity of 93% analyzed by gas chromatography.

The one or more epoxides employed in the reaction with the initiators to prepare the compounds of Formula I contain from 2 to 100 carbon atoms, preferably from 2 to 20 carbon atoms, more preferably from 2 to 4 carbon atoms, and most preferably four carbon atoms. The epoxides may be internal epoxides such as 2,3 epoxides of the formula:

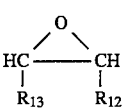
(XI)

wherein $R_{13}$ and $R_{12}$ are each independently hydrogen, hydrocarbyl, as defined hereinbefore, of 1 to 98 carbon atoms or substituted hydrocarbyl, as defined hereinbefore, of 1 to 98 carbon atoms or terminal epoxides such as 1,2 epoxides of the formula:

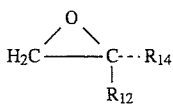

(XII)

wherein $R_{12}$ and $R_{14}$ are each independently hydrogen, hydrocarbyl, as defined hereinbefore, of 1 to 98 carbon atoms or substituted hydrocarbyl, as defined hereinbefore, of 1 to 98 carbon atoms. Preferably, $R_{12}$, $R_{13}$ and $R_{14}$ are each independently selected from hydrogen, hydrocarbyl of 2 to 48 carbon atoms and substituted hydrocarbyl of 2 to 48 carbon atoms, more preferably hydrogen, hydrocarbyl of 2 to 18 carbon atoms and substituted hydrocarbyl of 2 to 18 carbon atoms. Preferred compounds are those in which $R_{12}$, $R_{13}$ and $R_{14}$ are selected from hydrogen and hydrocarbyl of 1 to 2 carbon atoms, especially 2 carbon atoms. (Note that Formulas XII and XIII correspond to geminal and vicinal hydrocarbyls for $R_4$ and $R_5$. $R_{13}$ and $R_{12}$, or alternatively $R_{12}$ and $R_{14}$, may be taken together to form a cycloalkylene epoxide or a vinylidene epoxide by forming a divalent linking hydrocarbyl group of 3 to 12 carbon atoms.

When $R_{12}$, $R_{13}$ and/or $R_{14}$ are oxy-substituted hydrocarbyl, suitable compounds of Formulas XII and XIII will include compounds such as nonylphenyl glycidyl ether, phenyl glycidyl ether, cresyl glycidyl ether, butyl glycidyl ether, alkyl $C_{12}$–$C_{13}$ glycidyl ether, alkyl $C_8$–$C_{10}$ glycidyl ether, 2-ethylhexyl glycidyl ether and isopropyl glycidyl ether.

In the preferred embodiment, the terminal epoxides represented by Formula XIII are utilized to form amido derivatives. Ideally these terminal epoxides are 1,2-epoxyalkanes. Suitable 1,2-epoxyalkanes include 1,2-epoxyethane, 1,2-epoxypropane, 1,2-epoxybutane, 1,2-epoxydecane, 1,2-epoxydodecane, 1,2-epoxyhexadecane, 1,2-epoxyoctadecane and mixtures thereof.

In a typical preparation of Formula I compounds, the one or more epoxides and initiator are contacted at a ratio from about 7:1 to about 55:1 moles of epoxide per mole of initiator. Preferably, they are contacted at a molar ratio from about 10:1 to about 30:1, with the most preferred molar ratio being about 20:1.

The reaction is carried out in the presence of potassium compounds which act as alkoxylation catalysts. Such catalysts are conventional and include potassium methoxide, potassium ethoxide, potassium hydroxide, potassium hydride and potassium-t-butoxide. The preferred catalysts are potassium hydroxide and potassium-t-butoxide. The catalysts are used in a base stable solvent such as alcohol, ether or hydrocarbons. The catalysts are employed in a wide variety of concentrations. Generally, the potassium compounds will be used in an amount from about 0.02% to about 5.0% of the total weight of the mixture, preferably from about 0.1% to about 2.0% of the total weight of the mixture, and most preferably about 0.2% of the total weight of the mixture.

The reaction is conveniently carried out in a conventional autoclave reactor equipped with heating and cooling means. The process is practiced batchwise, continuously or semi-continuously.

The manner in which the alkoxylation reaction is conducted is not critical to the invention. Illustratively, the initiator and potassium compound are mixed and heated under vacuum for a period of at least 30 minutes. The one or more epoxides are then added to the resulting mixture, the reactor sealed and pressurized with nitrogen, and the mixture stirred while the temperature is gradually increased.

The temperature for alkoxylation is from about 80° C. to about 250° C., preferably from about 100° C. to about 150° C., and even more preferably from about 120° C. to about 140° C. The alkoxylation reaction time is generally from about 2 to about 20 hours, although longer or shorter times are employed.

Alkoxylation processes of the above type are known and are described, for example in U.S. Pat. Nos. 4,973,414, 4,883,826, 5,123,932 and U.S. Pat. No. 4,612,335, each incorporated herein by reference.

The product of Formula I is normally liquid and is recovered by conventional techniques such as filtration and distillation. The product is used in its crude state or is purified, if desired, by conventional techniques such as aqueous extraction, solid absorption and/or vacuum distillation to remove any remaining impurities.

Other methods for making the compounds of Formula I are known by those skilled in the art. For example, the compounds of Formula I are prepared by reacting an initiator as described hereinbefore with other cyclic ethers. In addition, other catalyst chemistry, such as the use of acidic catalysts, can be employed to achieve the compounds of Formula I.

Fuel Compositions

The compounds of Formula I are useful as additives in fuel compositions which are burned or combusted in internal combustion engines. The fuel compositions of the present invention comprise a major amount of a mixture of hydrocarbons in the gasoline boiling range and a minor amount of one or more of the compounds of Formula I. As used herein, the term "minor amount" means less than about 10% by weight of the total fuel composition, preferably less than about 1% by weight of the total fuel composition and more preferably less than about 0.1% by weight of the total fuel composition.

Suitable liquid hydrocarbon fuels of the gasoline boiling range are mixtures of hydrocarbons having a boiling range of from about 25° C. to about 232° C., and comprise mixtures of saturated hydrocarbons, olefinic hydrocarbons and aromatic hydrocarbons. Preferred are gasoline mixtures having a saturated hydrocarbon content ranging from about 40% to about 80% by volume, an olefinic hydrocarbon content from 0% to about 30% by volume and an aromatic hydrocarbon content from about 10% to about 60% by volume. The base fuel is derived from straight run gasoline, polymer gasoline, natural gasoline, dimer and trimerized olefins, synthetically produced aromatic hydrocarbon mixtures, or from catalytically cracked or thermally cracked petroleum stocks, and mixtures of these. The hydrocarbon composition and octane level of the base fuel are not critical. The octane level, (R+M)/2, will generally be above about 85.

Any conventional motor fuel base can be employed in the practice of the present invention. For example, hydrocarbons in the gasoline can be replaced by up to a substantial amount of conventional alcohols or ethers, conventionally known for use in fuels. The base fuels are desirably substantially free of water since water could impede a smooth combustion.

Normally, the hydrocarbon fuel mixtures to which the invention is applied are substantially lead-free, but may contain minor amounts of blending agents such as methanol, ethanol, ethyl tertiary butyl ether, methyl tertiary butyl ether, and the like, at from about 0.1% by volume to about 15% by volume of the base fuel, although larger amounts may be utilized. The fuels can also contain conventional additives including antioxidants such as phenolics, e.g., 2,6-di-tert-butylphenol or phenylenediamines, e.g., N,N'-di-sec-butyl-p-phenylenediamine, dyes, metal deactivators, dehazers such as polyester-type ethoxylated alkylphenol-formaldehyde resins. Corrosion inhibitors, such as a polyhydric alcohol ester of a succinic acid derivative having on at least one of its alpha-carbon atoms an unsubstituted or substituted aliphatic hydrocarbon group having from 20 to 500 carbon atoms, for example, pentaerythritol diester of polyisobutylene-substituted succinic acid, the polyisobutylene group having an average molecular weight of about 950, in an amount from about 1 parts per million (ppm) by weight to about 1000 ppm by weight, may also be present. The fuels can also contain antiknock compounds such as methyl cyclopentadienylmanganese tricarbonyl and orthoazidophenol as well as co-antiknock compounds such as benzoyl acetone.

An effective amount of one or more compounds of Formula I are introduced into the combustion zone of the engine in a variety of ways to prevent build-up of deposits, or to accomplish the reduction of intake valve deposits or the modification of existing deposits that are related to octane requirement. As mentioned, a preferred method is to add a minor amount of one or more compounds of Formula I to the fuel. For example, one or more compounds of Formula I are added directly to the fuel or are blended with one or more carriers and/or one or more additional detergents to form an additive concentrate which can be added at a later date to the fuel.

The amount of the one or more compounds of Formula I used will depend on the particular variation of Formula I used, the engine, the fuel, and the presence or absence of carriers and additional detergents. Generally, each compound of Formula I is added in an amount up to about 1000 ppm by weight, especially from about 1 ppm by weight to about 600 ppm by weight based on the total weight of the fuel composition. Preferably, the amount will be from about 50 ppm by weight to about 400 ppm by weight, and even more preferably from about 75 ppm by weight to about 250 ppm by weight based on the total weight of the fuel composition.

The carrier, when utilized, will have a weight average molecular weight from about 500 to about 5000. Suitable carriers, when utilized, include hydrocarbon based materials such as polyisobutylenes (PIB's), polypropylenes (PP's) and polyalphaolefins (PAO's); polyether based materials such as polybutylene oxides (poly BO's), polypropylene oxides (poly PO's), polyhexadecene oxides (poly HO's) and mixtures thereof (i.e., both (poly BO)+(poly PO) and (poly-BO-PO)); and mineral oils such as Exxon Naphthenic 900 sus and high viscosity index (HVI) oils. The carrier is preferably selected from PIB's, poly BO's, and poly PO's, with poly BO's being the most preferred.

The carrier concentration in the final fuel composition is up to about 1000 ppm by weight. When a carrier is present, the preferred concentration is from about 50 ppm by weight to about 400 ppm by weight, based on the total weight of the fuel composition. Once the carrier is blended with one or more compounds of Formula I, the blend is added directly to the fuel or packaged for future use.

The fuel compositions of the present invention may also contain one or more additional detergents. When additional detergents are utilized, the fuel composition will comprise a mixture of a major amount of hydrocarbons in the gasoline boiling range as described hereinbefore, a minor amount of one or more compounds of Formula I as described hereinbefore and a minor amount of an additional detergent selected from polyalkylenyl amines, Mannich amines, polyalkenyl succinimides, poly(oxyalkylene) carbamates, poly-(alkenyl)-N-substituted carbamates and mixtures thereof. As noted above, a carrier as described hereinbefore may also be included. As used herein, the term "minor amount" means less than about 10% by weight of the total fuel composition, preferably less than about 1% by weight of the total fuel composition and more preferably less than about 0.1% by weight of the total fuel composition.

The polyalkylenyl amine detergents utilized comprise at least one monovalent hydrocarbon group having at least 50 carbon atoms and at least one monovalent hydrocarbon group having at most five carbon atoms bound directly to separate nitrogen atoms of a diamine. Preferred polyalkylenyl amines are polyisobutenyl amines. Polyisobutenyl amines are known in the art and representative examples are disclosed in various U.S. Patents including U.S. Pat. Nos. 3,753,670, 3,756,793, 3,574,576 and 3,438,757, each incorporated herein by reference. Particularly preferred polyisobutenyl amines for use in the present fuel composition include N-polyisobutenyl-N',N'-dimethyl-1,3-diaminopropane (PIB-DAP) and OGA-472 (a polyisobutenyl ethylene diamine available commercially from Oronite).

The Mannich amine detergents utilized comprise a condensation product of a high molecular weight alkyl-substituted hydroxyaromatic compound, an amine which contains an amino group having at least one active hydrogen atom (preferably a polyamine), and an aldehyde. Such Mannich amines are known in the art and are disclosed in U.S. Pat. No. 4,231,759, incorporated herein by reference. Preferably, the Mannich amine is an alkyl substituted Mannich amine.

The polyalkenyl succinimide detergents comprise the reaction product of a dibasic acid anhydride with either a polyoxyalkylene diamine, a hydrocarbyl polyamine or mixtures of both. Typically the succinamide is substituted with the polyalkenyl group but the polyalkenyl group may be found on the polyoxyalkylene diamine or the hydrocarbyl polyamine. Polyalkenyl succinimides are also known in the art and representative examples are disclosed in various U.S. Patents including U.S. Pat. Nos. 4,810,261, 4,852,993, 4,968,321, 4,985,047, 5,061,291 and 5,147,414, each incorporated herein by reference.

The poly(oxyalkylene) carbamate detergents comprise an amine moiety and a poly(oxyalkylene) moiety linked together through a carbamate linkage, i.e.,

  (XIII)

These poly(oxyalkylene) carbamates are known in the art and representative examples are disclosed in various U.S. Patents including, U.S. Pat. Nos. 4,191,537, 4,160,648, 4,236,020, 4,270,930, 4,288,612 and 4,881,945, each incorporated herein by reference. Particularly preferred poly(oxyalkylene) carbamates for use in the present fuel composition include OGA-480 (a poly(oxyalkylene) carbamate which is available commercially from Oronite).

The poly(alkenyl)-N-substituted carbamate detergents utilized are of the formula:

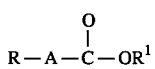  (XIV)

in which R is a poly(alkenyl) chain; $R^1$ is a hydrocarbyl or substituted hydrocarbyl group; and A is an N-substituted amino group. Poly(alkenyl)-N-substituted carbamates are known in the art and are disclosed in U.S. Pat. No. 4,936, 868, incorporated herein by reference.

The one or more additional detergents are added directly to the hydrocarbons, blended with one or more carriers, blended with one or more compounds of Formula I, or blended with one or more compounds of Formula I and one or more carriers before being added to the hydrocarbons.

The concentration of the one or more additional detergents in the final fuel composition is generally up to about 1000 ppm by weight for each additional detergent. When one or more additional detergents are utilized, the preferred concentration for each additional detergent is from about 50 ppm by weight to about 400 ppm by weight, based on the total weight of the fuel composition, even more preferably from about 75 ppm by weight to about 250 ppm by weight, based on the total weight of the fuel composition.

Engine Tests

Decreasing Intake Valve Deposits

The invention further provides a process for decreasing intake valve deposits in engines utilizing the compounds of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

By supplying to and combusting or burning the fuel composition in an internal combustion engine, deposits in the induction system, particularly deposits on the tulips of the intake valves, are reduced. The reduction is determined by running an engine with clean induction system components and pre-weighed intake valves on dynamometer test stands in such a way as to simulate road operation using a variety of cycles at varying speeds while carefully controlling specific operating parameters. The tests are run for a specific period of time on the fuel composition to be tested. Upon completion of the test, the induction system deposits are visually rated, the valves are reweighed and the weight of the valve deposits is determined.

Controlling Octane Requirement Increases

The invention further provides a process for controlling octane requirement increases in engines utilizing the compounds of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement is the maximum octane number of a gasoline that presents trace knock in a given engine within the engine's normal operating range. An increase in octane requirement is generally experienced during mileage accumulation on a new engine. The increase is typically attributed to an increase in engine deposits. Octane requirement increase control is a performance feature that is usually expressed as a comparison of the octane requirement increase developed with a gasoline containing additives (test gasoline) relative to a version of the same gasoline without additives (base gasoline), i.e., the positive difference obtained by subtracting the results of gasoline containing additives from gasoline which does not contain additives.

The test protocol for octane requirement increase control must establish the stable octane requirement of the base gasoline relative to a clean engine. Base gasoline is typically the test gasoline without additives or special treatment; however, it may be gasoline containing additives for a specific comparison.

Octane requirement increase control testing consists of operating an engine assembled with clean combustion chambers and induction system components on a test gasoline to octane stabilization, measuring the octane requirement at regular intervals. The octane requirement increase control is the difference between the stabilized octane requirement of the engine operated on test gasoline and that of the stabilized octane requirement of the engine on base gasoline.

Reduction of Octane Requirement

The invention still further provides a process for reducing octane requirement in engines utilizing the compounds of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement reduction is the reduction of the octane requirement of an engine by the action of a particular gasoline, usually measured as a decrease from a stabilized octane requirement condition.

Octane requirement reduction is a performance feature that demonstrates a reduction from the established octane requirement of a base gasoline in a given engine. Octane requirement reduction testing consists of operating an engine, which has achieved stable octane requirement using base gasoline, on a test gasoline for approximately 100 hours. Octane measurements are made daily and octane requirement reduction is a reduction of octane requirement from that of base gasoline. Several octane requirement reduction tests may be conducted in a series for fuel to fuel comparison, or test fuel to base fuel comparison, by restabilizing on base fuel between octane requirement reduction tests.

The contribution of specific deposits is determined by removing deposits of interest and remeasuring octane requirement immediately after the engine is warmed to operating temperature. The octane requirement contribution of the deposit is the difference in ratings before and after deposit removal.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

Examples

Compound Preparation

The cyclic amide compounds containing multiple polyether alcohol backbones used in the following examples were prepared by reacting an initiator with one or more epoxides in the presence of a potassium compound to produce compounds of Formula I having a weight average molecular weight from about 600 to about 4000. Weight average molecular weights (MW) were determined by gel permeation chromatography (GPC). Rotary evaporation under reduced pressure typically was conducted at a temperature from room temperature to 120° C.

Example 1

Step 1—Preparation of Initiator

A mixture of 2,7-dioxaspiro[4,4]nonane-1,6-dione (31.2 g, 0.2 mole) and ethanolamine (12.2 g) was placed in a round-bottomed flask equipped with a thermal couple, temperature controller, heating device, nitrogen inlet, stirrer and Dean-Stark Trap. The mixture was heated at 120° C.–130° C. for 4 hours. The progress of the reaction was monitored by the release of $CO_2$ by-products. After the reaction, the product was used without purification. The structure of the product was confirmed by IR and $C^{13}$ NMR.

Step 2—Butoxylation of Initiator

The Initiator of Step 1 (65 g, 0.37 mole) and potassium hydroxide (1.7 g in 1.7 g water) were mixed, subjected to rotary evaporation under reduced pressure and then charged along with 1,2-epoxybutane (535 g, 7.4 moles) into a one-liter autoclave reactor equipped with a heating device, temperature controller, mechanical stirrer and water cooling system. The autoclave reactor was purged of air with nitrogen and then pressurized to 50 psi with nitrogen at room temperature. The mixture was then heated to a temperature of 124° C.–140° C. for 9 hours. The autoclave reactor was cooled to room temperature and excess gas was vented. The crude product was subjected to rotary evaporation under reduced pressure, extracted with water and then subjected to rotary evaporation again. GPC analysis of the final product showed MW=1720 and a polydispersity of 1.17.

Test Results

In each of the following tests, the base fuel utilized comprised either premium unleaded gasoline (PU) (90+ octane, R+M/2]) and/or regular unleaded gasoline (RU) (85–88 octane, R+M/2]). Those skilled in the art will recognize that fuels containing heavy catalytically cracked stocks, such as most regular fuels, are typically more difficult to additize in order to control deposits and effectuate octane requirement reduction and octane requirement increase control. The compounds utilized were prepared as indicated by Example number and were used at the concentration indicated in ppm by weight. The tests employed are described below and the results of the various tests are set forth in the tables below.

Intake Valve Deposit Tests

Engines from vehicles were installed in dynamometer cells in such a way as to simulate road operation using a cycle of idle, low speed and high speed components while carefully controlling specific operating parameters. Fuels with and without the compounds of Formula I were tested in 3.3 L Dodges having port fuel injection to determine the effectiveness of the compounds of the present invention in reducing intake valve deposits ("L" refers to liter). Carbureted 0.359 L Honda generator engines were also utilized to determine the effectiveness of the compounds of the present invention in reducing intake valve deposits.

Before each test, the engine was inspected, the induction system components were cleaned and new intake valves were weighed and installed. The oil was changed and new oil and fuel filters, gaskets and spark plugs were installed.

In all engines except the Honda, the tests were run in cycles consisting of idle, 35 mph and 65 mph for a period of 100 hours unless indicated otherwise. In the Honda engines, the tests were run in cycles consisting of a no load idle mode for one minute followed by a three minute mode with a load at 2200 rpm's for a period of 40 hours unless indicated otherwise. At the end of each test, the intake valves were removed and weighed.

Results obtained using the compound of the present invention are included in the tables below. All tests of the compounds of the present invention were carried out with additive concentrations (the amount of Compound Example # used) of 200 ppm non-volatile matter (nvm). Base Fuel results which have 0 ppm additive are also included for comparison purposes. The base fuels are indicated by the absence of a Compound Example # (indicated in the Compound Example # column by —).

TABLE 2

| Intake Valve Deposits in Honda Generator Engines | | | | |
|---|---|---|---|---|
| Compound Example # | Fuel | Compound Dosage | Engine | Avg. Deposit Wt. (mg) |
| 1 | PU | 200 | H2C | 31.0 |
| — | " | 0 | " | 57.1 |
| 1 | PU | 200 | H3C | 16.9 |
| — | " | 0 | * | 33.2 |

—Indicates the results achieved with base fuel in the absence of any additive compound (0 ppm additive compound).
*Indicates that this was an average of 4 runs in the same base fuel in other Honda generator engines.

TABLE 3

| Intake Valve Deposits in Various Engines | | | | |
|---|---|---|---|---|
| Compound Example # | Engine | Fuel | Concentration ppm By Wt | Avg. Deposit Wt (mg) |
| 1 | 3.3 L DODGE | PU | 200 | 159.7 |
| — | 3.3 L DODGE | * | 0 | 150.0 |

—Indicates the results achieved with base fuel in the absence of any additive compound (0 ppm additive compound).
*Indicates that this was an average of 3 runs of similar base fuels in the same engine (3.3 L Dodge).

What is claimed is:

1. A fuel composition comprising a mixture of a major amount of hydrocarbons in the gasoline boiling range and a minor amount of an additive compound having the formula:

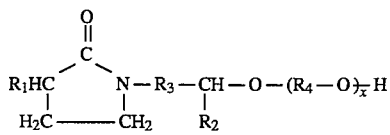

wherein $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

$$-(R_5-O)_{\overline{y}}H$$

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selected from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; x is from 1 to 50; and the weight average molecular weight of the additive compound is at least 600.

2. The fuel composition of claim 1 wherein said additive compound is present in an amount from about 50 ppm by weight to about 400 ppm by weight based on the total weight of the fuel composition.

3. The fuel composition of claim 2 wherein the weight average molecular weight of the additive compound is from about 800 to about 4000.

4. The fuel composition of claim 3 wherein $R_1$ is polyoxyalkylene alcohol and $R_5$ is hydrocarbyl of the formula:

$$-CH_2-\underset{\underset{R_6}{|}}{\overset{\overset{R_8}{|}}{C}}-$$

wherein each $R_8$ is independently selected from hydrogen, hydrocarbyl of 1 to 18 carbon atoms and substituted hydrocarbyl of 1 to 18 carbon atoms and each $R_6$ is independently selected from hydrogen, hydrocarbyl of 1 to 18 carbon atoms and substituted hydrocarbyl of 1 to 18 carbon atoms.

5. The fuel composition of claim 4 wherein $R_4$ is hydrocarbyl of the formula:

$$-CH_2-\underset{\underset{R_9}{|}}{\overset{\overset{R_{11}}{|}}{C}}-$$

wherein each $R_{11}$ is independently selected from hydrogen, hydrocarbyl of 1 to 18 carbon atoms and substituted hydrocarbyl of 1 to 18 carbon atoms and each $R_9$ is independently selected from hydrogen, hydrocarbyl of 1 to 18 carbon atoms and substituted hydrocarbyl of 1 to 18 carbon atoms.

6. The fuel composition of claim 5 wherein each $R_3$ is independently selected from hydrocarbyl comprising alkyl of 1 to 20 carbon atoms.

7. The fuel composition of claim 5 wherein each $R_3$ is independently selected from hydrocarbyl comprising alkyl of 1 to 3 carbon atoms and $R_2$ is hydrogen.

8. The fuel composition of claim 6 wherein $R_8$ is hydrogen; each $R_6$ is independently selected from hydrogen and hydrocarbyl comprising alkyl of 1 to 2 carbon atoms; $R_{11}$ is hydrogen; each $R_9$ is independently selected from hydrogen and hydrocarbyl comprising alkyl of 1 to 2 carbon atoms; and $R_2$ is hydrogen.

9. The fuel composition of claim 8 wherein x is from 1 to 26 and y is from 1 to 26.

10. The fuel composition of claim 7 wherein $R_8$ is hydrogen; each $R_6$ is independently selected from hydrogen and hydrocarbyl comprising alkyl of 1 to 2 carbon atoms; $R_{11}$ is hydrogen; and each $R_9$ is independently selected from hydrogen and hydrocarbyl comprising alkyl of 1 to 2 carbon atoms.

11. The fuel composition of claim 10 wherein x is from 1 to 26 and y is from 1 to 26.

12. The fuel composition of claim 2 wherein $R_1$ is polyoxyalkylene alcohol and $R_5$ is hydrocarbyl of the formula:

$$-\underset{\underset{R_7}{|}}{CH}-\underset{\underset{R_8}{|}}{CH}-$$

wherein each $R_7$ is independently selected from hydrogen, hydrocarbyl of 1 to 18 carbon atoms and substituted hydrocarbyl of 1 to 18 carbon atoms and each $R_8$ is independently selected from hydrogen, hydrocarbyl of 1 to 18 carbon atoms and substituted hydrocarbyl of 1 to 18 carbon atoms.

13. The fuel composition of claim 12 wherein $R_4$ is hydrocarbyl of the formula:

$$-\underset{\underset{R_{10}}{|}}{CH}-\underset{\underset{R_9}{|}}{CH}-$$

wherein each $R_{10}$ is independently selected from hydrogen, hydrocarbyl of 1 to 18 carbon atoms and substituted hydrocarbyl of 1 to 18 carbon atoms and each $R_9$ is independently selected from hydrogen, hydrocarbyl of 1 to 18 carbon atoms and substituted hydrocarbyl of 1 to 18 carbon atoms.

14. The fuel composition of claim 13 wherein each $R_3$ is independently selected from hydrocarbyl comprising alkyl of 1 to 20 carbon atoms; x is from 1 to 26 and y is from 1 to 26.

15. A method for reducing intake valve deposits in an internal combustion engine which comprises burning in said engine a fuel composition comprising a mixture of a major amount of hydrocarbons in the gasoline boiling range and a minor amount of an additive compound having the formula:

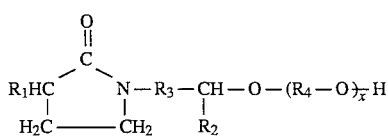

wherein $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

$$-(R_5-O)_{\overline{y}}H$$

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selcted from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; x is from 1 to 50; and the weight average molecular weight of the additive compound is at least 600.

16. The fuel composition of claim 15 wherein said additive compound is present in an amount from about 50 ppm by weight to about 400 ppm by weight based on the total weight of the fuel composition.

17. The method of claim 16 wherein the weight average molecular weight of the additive compound is from about 800 to about 4000.

18. The method of claim 17 wherein $R_1$ is polyoxyalkylene alcohol and $R_5$ is hydrocarbyl of the formula:

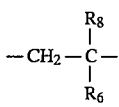

wherein each $R_8$ is independently selected from hydrogen, hydrocarbyl of 1 to 18 carbon atoms and substituted hydrocarbyl of 1 to 18 carbon atoms and each $R_6$ is independently selected from hydrogen, hydrocarbyl of 1 to 18 carbon atoms and substituted hydrocarbyl of 1 to 18 carbon atoms.

19. The method of claim 18 wherein $R_4$ is hydrocarbyl of the formula:

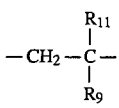

wherein each $R_{11}$ is independently selected from hydrogen, hydrocarbyl of 1 to 18 carbon atoms and substituted hydrocarbyl of 1 to 18 carbon atoms and each $R_9$ is independently selected from hydrogen, hydrocarbyl of 1 to 18 carbon atoms and substituted hydrocarbyl of 1 to 18 carbon atoms.

20. The method of claim 19 wherein each $R_3$ is independently selected hydrocarbyl comprising alkyl of 1 to 20 carbon atoms.

21. The method of claim 19 wherein each $R_3$ is independently selected hydrocarbyl comprising alkyl of 1 to 3 carbon atoms and $R_2$ is hydrogen.

22. The method of claim 20 wherein $R_8$ is hydrogen; each $R_6$ is independently selected from hydrogen and hydrocarbyl comprising alkyl of 1 to 2 carbon atoms; $R_{11}$ is hydrogen; each $R_9$ is independently selected from hydrogen and hydrocarbyl comprising alkyl of 1 to 2 carbon atoms; and $R_2$ is hydrogen.

23. The method of claim 22 wherein x is from 1 to 26 and y is from 1 to 26.

24. The method of claim 21 wherein $R_8$ is hydrogen; each $R_6$ is independently selected from hydrogen and hydrocarbyl comprising alkyl of 1 to 2 carbon atoms; $R_{11}$ is hydrogen; each $R_9$ is independently selected from hydrogen and hydrocarbyl comprising alkyl of 1 to 2 carbon atoms; and $R_2$ is hydrogen.

25. The method of claim 24 wherein x is from 1 to 26 and y is from 1 to 26.

26. A method for controlling the octane requirement increase in an internal combustion engine which comprises burning in said engine a fuel composition comprising a mixture of a major amount of hydrocarbons in the gasoline boiling range and a minor amount of an additive compound having the formula:

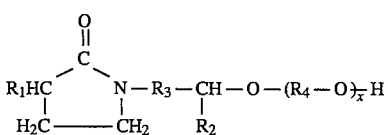

wherein $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

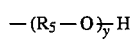

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selcted from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; x is from 1 to 50; and the weight average molecular weight of the additive compound is at least 600.

27. A method for reducing octane requirement in an internal combustion engine which comprises burning in said engine a fuel composition comprising a mixture of a major amount of hydrocarbons in the gasoline boiling range and a minor amount of an additive compound having the formula:

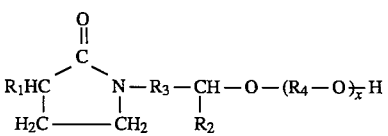

wherein $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

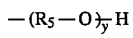

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selcted from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; x is from 1 to 50; and the weight average molecular weight of the additive compound is at least 600.

28. A compound of the formula:

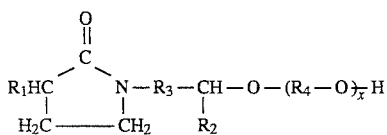

wherein $R_5$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

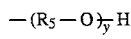

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$; is selected from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; and x is from 1 to 50.

29. The compound of claim 26 wherein $R_1$ is polyoxyalkylene alcohol and $R_5$ is hydrocarbyl of the formula:

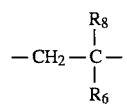

wherein each $R_8$ is independently selected from hydrogen, hydrocarbyl of 1 to 18 carbon atoms and substituted hydrocarbyl of 1 to 18 carbon atoms and each $R_6$ is independently selected from hydrogen, hydrocarbyl of 1 to 18 carbon atoms and substituted hydrocarbyl of 1 to 18 carbon atoms.

30. The compound of claim 27 wherein $R_4$ is hydrocarbyl of the formula:

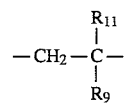

wherein each $R_{11}$ is independently selected from hydrogen, hydrocarbyl of 1 to 18 carbon atoms and substituted hydrocarbyl of 1 to 18 carbon atoms and each $R_9$ is independently selected from hydrogen, hydrocarbyl of 1 to 18 carbon atoms and substituted hydrocarbyl of 1 to 18 carbon atoms.

31. The compound of claim 28 wherein each $R_3$ is independently selected from hydrocarbyl comprising alkyl of 1 to 20 carbon atoms.

32. The compound of claim 29 wherein each $R_3$ is independently selected from hydrocarbyl comprising alkyl of 1 to 3 carbon atoms and $R_2$ is hydrogen.

33. The compound of claim 29 wherein $R_8$ is hydrogen; each $R_6$ is independently selected from hydrogen and hydrocarbyl comprising alkyl of 1 to 2 carbon atoms; $R_{11}$ is hydrogen; each $R_9$ is independently selected from hydrogen and hydrocarbyl comprising alkyl of 1 to 2 carbon atoms; and $R_2$ is hydrogen.

34. The compound of claim 31 wherein x is from 1 to 26 and y is from 1 to 26.

35. The compound of claim 30 wherein $R_8$ is hydrogen; each $R_6$ is independently selected from hydrogen and hydrocarbyl comprising alkyl of 1 to 2 carbon atoms; $R_{11}$ is hydrogen; each $R_9$ is independently selected from hydrogen and hydrocarbyl comprising alkyl of 1 to 2 carbon atoms; and $R_2$ is hydrogen.

36. The method of claim 33 wherein x is from 1 to 26 and y is from 1 to 26.

37. A fuel composition comprising a mixture of:
(a) a major amount of hydrocarbons in the gasoline boiling range;
(b) a minor amount of an additive compound having the formula:

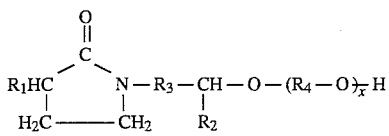

wherein $R_1$ and $R_2$ are each independently selected from the group consisting of hydrogen, hydrocarbyl of 1 to 100 carbon atoms, substituted hydrocarbyl of 1 to 100 carbon atoms and polyoxyalkylene alcohol of the formula:

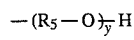

wherein each $R_5$ is independently selected from hydrocarbyl of 2 to 100 carbon atoms and substituted hydrocarbyl of 2 to 100 carbon atoms and y is from 1 to 50 with the proviso that at least one of $R_1$ and $R_2$ must be polyoxyalkylene alcohol; $R_3$ is selected from the group consisting of hydrocarbyl of 1 to 100 carbon atoms and substituted hydrocarbyl of 1 to 100 carbon atoms; each $R_4$ is independently selected from hydrocarbyl of 1 to 100 carbon atoms and substituted hydrocarbyl of 1 to 100 carbon atoms; and x is from 1 to 50; and the weight average molecular weight of the additive compound is at least about 600; and (c) a minor amount of an additional detergent selected from the group consisting of polyalkylenyl amines, mannich amines, polyalkenyl succinimides, poly(oxyalkylene) carbamates, poly(alkenyl)-N-substituted carbamates and mixtures thereof.

* * * * *